United States Patent [19]

Viera

[11] Patent Number: 5,363,847
[45] Date of Patent: Nov. 15, 1994

[54] GUIDEWIRE HAVING DOUBLE DISTAL PORTIONS

[75] Inventor: Fernando M. Viera, Hialeah, Fla.

[73] Assignee: Cordis Corporation, Miami Lakes, Fla.

[21] Appl. No.: 144,058

[22] Filed: Oct. 27, 1993

[51] Int. Cl.⁵ ............................................... A61B 6/00
[52] U.S. Cl. .................................. 128/657; 128/772; 604/264; 604/280
[58] Field of Search ....................... 128/657, 658, 772; 604/95, 164, 170, 264, 280

[56] References Cited

U.S. PATENT DOCUMENTS

| | | | |
|---|---|---|---|
| 4,721,117 | 1/1988 | Mar et al. | 604/164 |
| 4,763,647 | 8/1988 | Gambale . | |
| 4,846,186 | 7/1989 | Box et al. . | |
| 4,867,173 | 9/1989 | Leoni . | |
| 4,921,483 | 5/1990 | Wijay et al. . | |
| 4,991,602 | 2/1991 | Amplatz et al. | 604/164 |
| 5,120,308 | 6/1992 | Hess | 604/96 |
| 5,209,735 | 5/1993 | Lazarus . | |
| 5,243,996 | 9/1993 | Hall | 604/95 |
| 5,247,942 | 9/1993 | Prather et al. . | |

Primary Examiner—C. Fred Rosenbaum
Assistant Examiner—N. Kent Gring
Attorney, Agent, or Firm—Gerstman, Ellis & McMillin, Ltd.

[57] ABSTRACT

An intravascular guidewire is provided having a central section which typically comprises the majority of the length of the guidewire, and terminal sections which are of lesser diameter than the diameter of the central section. Each of the terminal sections is of differing physical characteristics relative to each other, to exhibit differing dynamic characteristics during use. This provides the user with a greater variety of guidewire performance characteristics, depending upon which end of the guidewire is used as the distal end of advancement.

6 Claims, 1 Drawing Sheet

GUIDEWIRE HAVING DOUBLE DISTAL PORTIONS

BACKGROUND OF THE INVENTION

Guidewires are used as part of the process to facilitate the advancement of vascular catheters such as angiography or angioplasty catheters through the vascular system of a patient, typically into the coronary arteries. The guidewire provides a track along which a catheter may be advanced, after the guidewire has successfully negotiated the labyrinth of blood vessels through which it may have to pass through in order to reach a desired site. The catheter thus only has to subsequently follow the track of the guidewire, which it tends to do in spontaneous manner as it is advanced.

Different guidewires are available to provide differing performance characteristics, depending upon the particular clinical need of the situation. Some guidewires are very flexible and capable of negotiating tight curves in the coronary arteries. Other guidewires are stiffer for greater pushability, with their physical characteristics being governed by their diameters, material compositions, and the like.

Particularly, the distal end of the guidewire is critical as to its physical characteristics, with the distal end often being of more flexibility than the central portion of the guidewire, the dimensions and design being proportioned to give the desired characteristics of flexibility to the distal end.

Frequently, it turns out that a guidewire which is being advanced through the arterial system of the patient is not of optimum physical characteristics to negotiate a certain internal area which the distal tip of the guidewire reaches after substantial advancement, In this circumstance, a catheter may be advanced along the guidewire. Then, the guidewire is withdrawn and replaced through the catheter with another guidewire of more desireable physical characteristics. Thus, in an angioplasty or angiographic procedure, two or more guidewires may be used in sequential order.

DESCRIPTION OF THE INVENTION

In accordance with this invention, a guidewire is provided having two ends, either of which may be used as the distal guidewire end, with each end of the guidewire having differing physical characteristics.

Thus, the guidewire may be used in conventional manner, with one end being presented as the distal end. Then, in the event of clinical need for a guidewire of differing characteristics, the guidewire may be withdrawn, reversed, and advanced with its opposite end serving as the distal end. This opposite end has differing physical characteristics perhaps due to a different diameter and/or length, or an array of differing diameters, and/or differing lengths, and/or the use of different alloys, so that the same guidewire may serve as a guidewire providing a choice of two different physical characteristics at its distal end. This makes possible the use of a single guidewire in a complex clinical procedure, where in the past two, separate guidewires had to be used, resulting in significant convenience as well as a significant reduction in cost.

Typically, the guidewires of this invention exhibit a tip at one or both-ends which is of larger diameter than a subsequent, narrow-diameter section between the tip and the remainder of the guidewire. Then, inwardly of that, portions may be provided in which the diameter of the guidewire expands as one moves toward the center to connect with a constant-diameter guidewire length. Travelling further inwardly, another expanding-diameter guidewire section may be provided, to serve as a transition zone for the connection between the constant-diameter guidewire length mentioned and a more central guidewire portion of larger diameter. A spring may surround this tip. The tip and spring may be relatively long, for example about 23 cm.

Other guidewires may have one or both ends which are of substantially constant diameter with the central guidewire portion, except for a short, reduced-diameter tip section of 3 cm. or so, typically surrounded by a short spring, plus an optional proximal Teflon plastic sleeve.

Either or both of the above tip structures, which per se are in the prior art, may be found at the respective ends of the guidewire, with the end portions having differing dimensions of design, length, diameter, and/or alloy composition as desired, to provide differing dynamic characteristics for the respective guidewire ends in terms of the ability to negotiate curves and the overall pushability, which is a function in part of the stiffness of the guidewire. When outer springs are used at the guidewire ends, they also may provide all or part of the variability between ends in accordance with this invention.

Thus, the surgeon has a single guidewire which exhibits doubled versatility of use, reducing the need for a second guidewire in many circumstances.

DESCRIPTION OF SPECIFIC EMBODIMENTS

Figure 1:
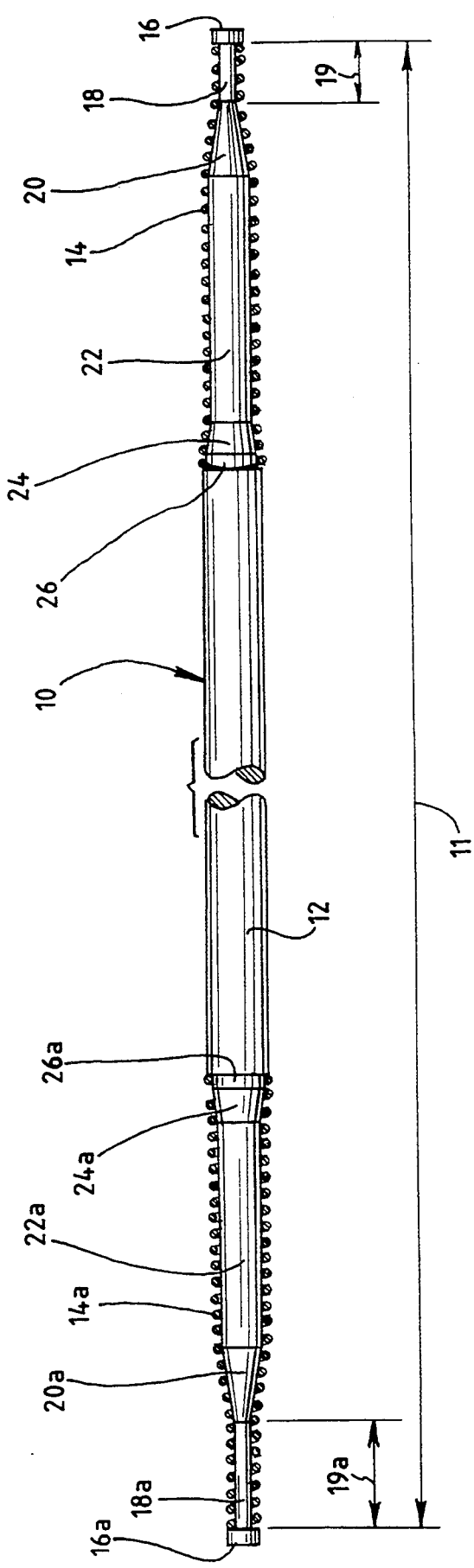
FIG. 1 is a fragmentary, plan view showing both ends of an otherwise conventional guidewire for use in angioplasty and angiography.

Referring to FIG. 1, guidewire 10 may be of generally conventionally design except as otherwise indicated herein, having a length 11, for example, of about 80 to 81 inches, specifically, 80.86 inches. Most of the length of the guidewire comprises a central section 12 having a diameter of 0.013 inch, for example.

Guidewire 10 may carry outer spring members 14, 14a adjacent to its respective ends in conventional manner. Both springs 14, 14a and the guidewire 10 may be made of conventional alloys, which may differ from end to end to provide added variable characteristics to the respective tips.

At the respective ends of guidewire 10 there is a relatively enlarged, short first segment or tip 16, 16a, each of which may have a diameter of about 0.0035 to 0.004 inch, and a length along the axis of the guidewire of about 0.02 to 0.04 inch. Specifically segment 16 may have a diameter of 0.0040 inch and a length of 0.03 inch.

The respective guidewire tips 16, 16a are integrally connected to a thinner length of the guidewire 18, 18a, each of which are preferably of differing dimensions from each other. Specifically, this second guidewire section 18 may have a diameter of 0.0025 to 0.0028 inch and a length 19 of 0.5 to 0.7 inch, specifically, 0.6 inch. On the other hand, corresponding second section 18a at the other guidewire end may be of similar diameter but may have a length 19a of 1.1 to inch, specifically 1.2 inch.

The guidewire has first conical transition sections 20, 20a adjacent each end, providing a conical transition between second sections 18, 18a and third sections 22, 22a. These first conical transition segments may have varying lengths, with appropriate variation of the conical angle of the sides thereof. The length of conical segment 20 may be from 1.9 to 2.1 inches, specifically being 2.0 inches in this embodiment. The length of conical segment 20a may be 3.1-3.3 inches, specifically 3.2 inches.

Thus, it can be seen that the respective dynamic characteristics of sections 18 and 20 are going to be different from the corresponding characteristics of segments 18a and 20a, because of the differing dimensions thereof.

Second segment 22 may have a diameter of 0.0072 to 0.0075 inch, the specific diameter shown being the former value. The length of second segment 22 may be about 6.4 to 6.8 inches, specifically 6.2 inches.

The corresponding second segment 22a may have a diameter of 0.007 to 0.0073 inch, preferably being different in diameter from segment 22. The length of segment 22a may be 6.8 to 7.2 inches, specifically 7.0 inches. This also is typically different from the length of segment 22, although the respective segments may, if desired vary in only one dimension, or not at all, relying upon the differences between other segments in the guidewire. Also the difference between the respective segments or sections may be in the alloy composition.

The guidewire has second conical transition segments 24, 24a to accommodate the differing diameters of segments 22, 22a with respect to the diameter of central, long segment 12. The length of conical segment 24 may be about 0.77 to 0.98 inch, typically about 0.875 inch. The length of conical segment 24a may be about 0.97 to 1.18 inch, typically about 1.075 inch.

Also, a small, cylindrical segment 26, 26a is provided, both of these cylindrical segments having a diameter of about 0.0105 to 0.01053 inch, which also is the maximum diameter of second conical transition segments 24, 24a. A step, 28, 28a is provided between segments 26, 26a and the central, major segment 12 to serve as a seat for one end of springs 14, 14a. The other spring ends seat by end tips 16, 16a. Segments 26, 26a may be about 0.123 to 0.127 inch in length, typically about 0.125 inch.

Springs 14, 14a may have different lengths, corresponding to the sections they enclose.

Thus, a guidewire is provided having end portions which exhibit different dynamic characteristics with respect to bendability, trackability, and pushability, to give various and different desired characteristics in the handling of the guidewire, depending upon which end thereof is serving as the distal, advancing end. By this means, the surgeon can use a single guidewire in a more versatile manner, which can provide both added convenience of use and reduced cost to the medical procedure.

The above has been offered for illustrative purposes only, and is not intended to limit the scope of the invention of this application, which is as defined in the claims below.

That which is claimed is:

1. An intravascular guidewire which comprises a length of wire having a pair of opposed end wire portions, the end wire portions of said guidewire each having a different stiffness relative to each other, to exhibit differing dynamic characteristics during use, a central portion being present in said guidewire, said central portion being of greater diameter than said end wire portions, said central portion comprising the majority of the length of said guidewire.

2. The guidewire of claim 1 in which each end wire portion comprises a plurality of segments of differing dimensions, said segments being of lesser diameters than the diameter of said central portion.

3. The guidewire of claim 1 in which each end wire portion of said guidewire carries an outer spring member, each of a different length to the other, surrounding at least the majority of each end wire portion.

4. The guidewire of claim 1 in which each end wire portion is of differing dimension relative to each other.

5. An intravascular guidewire which comprises a length of wire having a pair of opposed end wire portions of reduced diameter compared to a central portion thereof, the end wire portions of said guidewire each being of differing dimension relative to each other, to exhibit differing dynamic characteristics during use, said central portion comprising a majority of the length of said guidewire, each end wire portion comprising a plurality of segments of differing dimensions, said segments being of lesser diameters than the diameter of said central portion.

6. The guidewire of claim 5 in which each end wire portion of said guidewire carries an outer spring member, each of a different length to the other surrounding at least the majority of each end wire portion.

* * * * *